United States Patent [19]

Tamaki et al.

[11] Patent Number: 4,847,286
[45] Date of Patent: Jul. 11, 1989

[54] CROMOGLYCIC ACID DERIVATIVES, METHOD OF PRODUCTION THEREOF AND PHARMACEUTICAL COMPOSITION

[75] Inventors: Satoshi Tamaki, Moriyama; Masaru Kitagawa, Kyoto; Hirokazu Tsuda, Nara; Susumu Nishizawa, Kyoto; Nobuhara Kakeya, Nagaokakyo; Kazuhiko Kitao, Kyoto, all of Japan

[73] Assignee: Kyoto Pharmaceutical Industries, Ltd., Japan

[21] Appl. No.: 46,882

[22] PCT Filed: Aug. 13, 1986

[86] PCT No.: PCT/JP86/00415

§ 371 Date: Mar. 27, 1987

§ 102(e) Date: Mar. 27, 1987

[87] PCT Pub. No.: WO87/01115

PCT Pub. Date: Feb. 26, 1987

[30] Foreign Application Priority Data

Aug. 16, 1985 [JP] Japan ................. 60-180700

[51] Int. Cl.$^4$ ................. A61K 31/35; C07D 311/24
[52] U.S. Cl. .................. 514/456; 549/402; 549/305; 549/229; 514/467; 514/470
[58] Field of Search .............. 549/402, 305, 229; 514/456, 467, 470

[56] References Cited

U.S. PATENT DOCUMENTS 4,028,415  6/1977  Clark ........................ 560/173
4,189,571  2/1980  Bodor et al. ............... 549/402

OTHER PUBLICATIONS

Bodor et al., C.A., 94, 180,605y (1980).

Primary Examiner—Nicky Chan
Attorney, Agent, or Firm—Berman, Aisenberg & Platt

[57] ABSTRACT

Cromoglycic acid derivatives of the general formula

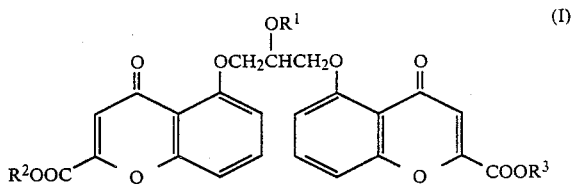

wherein $R^1$ is an $\alpha$-, $\beta$- or $\gamma$-amino acid residue (for ester bonding) whose amino group may optionally be substituted by at least one lower alkyl group, and $R^2$ and $R^3$ each independently is a lower alkyloxy-substituted or an unsubstituted lower alkyl group, an 1-alkanoyloxyalkyl group, an 1-alkoxycarbonyloxyalkyl group, a phthalidyl group or a 5-methyl-1,3-dioxol-2-on-4-ylmethyl group; nontoxic salts thereof; and pharmaceutical compositions containing such compounds. Since the compounds have antiallergic activity and are readily absorbable into the blood stream, they are useful as oral antiallergic agents.

8 Claims, No Drawings

CROMOGLYCIC ACID DERIVATIVES, METHOD OF PRODUCTION THEREOF AND PHARMACEUTICAL COMPOSITION

FIELD OF ART

This invention relates to cromoglycic acid derivatives and nontoxic salts thereof and pharmaceutical compositions, for example antiallergic compositions, containing the same.

BACKGROUND ART

So far, the compound of formula (II):

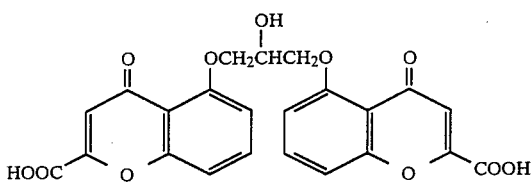

[hereinafter sometimes referred to as "cromoglycic acid (II)"], which has antiallergic activity, has been used as an antiallergic agent generally in its sodium salt form.

Since it cannot be absorbed in the digestive tract, cromoglycic acid (II) has been administered generally by spraying for inhalation into the nostrils or oral cavity using a sprayer for exclusive use for that purpose.

However, this method of administration is disadvantageous in that difficulties in connection with the operation of the sprayer are encountered in the process of inhalation (especially in young children and the aged).

Therefore, development of cromoglycic acid derivatives absorbable even after oral administration has been earnestly desired.

Accordingly, it is a primary object of the invention to provide cromoglycic acid derivatives which are orally administrable and have high antiallergic activity.

A second object of the invention is to provide a method of producing the noted derivatives.

A third object of the invention is to provide pharmaceutical compositions, for example antiallergic compositions for oral application, which contain said compounds.

DISCLOSURE OF THE INVENTION

As a result of their investigation in search of orally administrable, novel cromoglycic acid derivatives, the present inventors found that the cromoglycic acid derivatives (I) defined hereinbelow are superior in absorbability through the digestive tract and, after absorption, are rapidly converted to the cromoglycic acids (II) (hereinafter sometimes referred to as "non-ester forms") as a result of in vivo enzymatic hydrolysis of the respective ester moieties, which means that oral administration of the cromoglycic acid derivatives (I) results in high blood levels of the non-ester forms which have excellent antiallergic activity, and hence results in prolonged maintenance of said antiallergic activity. The present inventors also found that conversion of the cromoglycic acid derivatives (I) to their acid addition salts increases the efficiency of absorption and at the same time contributes to the stabilization of the cromoglycic acid derivatives (I) and facilitates the isolation procedure and the manufacture of orally administrable preparations. Furthermore, they found that oral administration of the cromoglycic acid derivatives (I) in the presence of an organic acid results in substantial increases in the solubility of the cromoglycic acid derivatives (I) in the digestive tract. The above findings and the establishment of a method of producing the cromoglycic acid derivatives (I) have now led to completion of the present invention.

Thus, the present invention relates to compounds of the general formula (I) [i.e. cromoglycic acid derivatives (I)]:

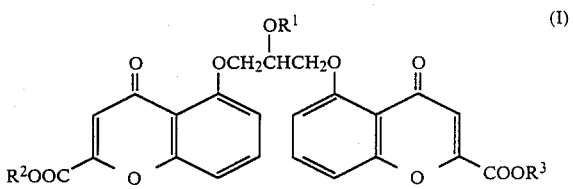

wherein $R^1$ is an $\alpha$-, $\beta$- or $\gamma$-amino acid residue (for ester bonding) whose amino group may optionally be substituted by at least one lower alkyl group, and each of $R^2$ and $R^3$ is, independently, a lower alkyloxy-substituted or an unsubstituted lower alkyl group, a 1-alkanoyloxyalkyl group, a 1-alkoxycarbonyloxyalkyl group, a phthalidyl group or a 5-methyl-1,3-dioxol-2-on-4-ylmethyl group and nontoxic salts thereof.

The invention also relates to a method of producing the cromoglycic acid derivatives (I) which comprises reacting a compound of the general formula (III) with a compound of the general formula (IV) given hereinbelow.

The invention further relates to antiallergic agents which contain the cromoglycic acid derivatives (I) or nontoxic salts thereof as active ingredients.

Referring to $R^1$ in general formula (I), the amino acid residue forms an ester bond with the adjacent oxygen atom and is an $\alpha$-, $\beta$- or $\gamma$-amino acid residue. The amino group of said amino acid residue may optionally be substituted by at least one lower alkyl, for example a $C_{1-4}$ lower alkyl, such as methyl, ethyl, propyl, iso-propyl or butyl. Such amino acid residue may be in the D, L or DL form and further may be in the form of a peptide composed of two or more amino acids. Examples of such amino acid residues are as follows:

Neutral amino acid residues:

Aliphatic amino acid residues [glycyl, alanyl, valyl, leucyl, isoleucyl, etc.], hydroxyamino acid residues [seryl, threonyl, etc.], sulfur-containing amino acid residues [cysteinyl, cystyl, methionyl, etc.], amidoamino acid residues [asparaginyl, glutaminyl, etc.], aromatic amino acid residues [phenylalanyl, tyrosyl, tryptophyl, etc.], and so on;

Acidic amino acid residues:

Aspartyl, glutamyl, etc.;

Basic amino acid residues:

Histidyl, lysyl, arginyl, etc.;

Imino acid residues:

Prolyl, hydroxyprolyl, etc.;

Amino acid residues other than $\alpha$-amino acid residues:

$\beta$-Alanyl, $\gamma$-aminobutyryl, etc.;

N-substituted amino acid residues:

Sarcosyl, N,N-dimethylglycyl, etc.; and

Peptide residues:

Glycylglycyl, alanylglycyl, leucylglycyl, etc.

Referring to $R^2$ and $R^3$ in general formula (I), the term "lower alkyl" means a straight or branched alkyl group containing 1-6 carbon atoms, such as methyl, ethyl, propyl, isopropyl, n-butyl, isobutyl, t-butyl, n-pentyl or n-hexyl.

The alkanoyl moiety of the 1-alkanoyloxyalkyl group represented by $R^2$ and/or $R^3$ contains 1-10 carbon atoms, preferably 1-7 carbon atoms, and the alkyl moiety contains 1-4 carbon atoms, preferably 1-2 carbon atoms. As such group, there may be mentioned, for example, acetoxymethyl, propionyloxymethyl, n-butyryloxymethyl, isobutyryloxymethyl, pivaloyloxymethyl, n-valeryloxymethyl, 2-methylbutynyloxymethyl, isovaleryloxymethyl, n-hexanoyloxymethyl, 3-methylvaleryloxymethyl, neohexanoyloxymethyl, 2-methylhexanoyloxymethyl, 2,2-dimethylbutyryloxymethyl, diethylacetoxymethyl, dipropylacetoxymethyl, 2,2-dimethylvaleryloxymethyl, neoheptanoyloxymethyl, cyclohexanoyloxymethyl, cyclohexylacetoxymethyl, 1-acetoxyethyl, 1-n-propionyloxyethyl, 1-n-butyryloxyethyl, 1-isobutyryloxyethyl, 1-n-valeryloxyethyl, 1-pivaloyloxyethyl, 1-isovaleryloxyethyl, 1-n-hexanoyloxyethyl and 1-cyclohexanoyloxyethyl.

The alkoxy moiety of the alkoxycarbonyloxyalkyl group represented by $R^2$ and/or $R^3$ contains 1-10 carbon atoms, preferably 1-7 carbon atoms, and the alkyl moiety contains 1-3 carbon atoms, preferably 2 carbon atoms. As such group, there may be mentioned, for example, 1-methoxycarbonyloxyethyl, 1-ethoxycarbonyloxyethyl, 1-n-propoxycarbonyloxyethyl, 1-isopropoxycarbonyloxyethyl, 1-n-butoxycarbonyloxyethyl, 1-tert-butoxycarbonyloxyethyl, 1-pentyloxycarbonyloxyethyl and 1-hexyloxycarbonyloxyethyl.

As examples of $R^2$ and $R^3$ which are preferable, there may be mentioned methyl, ethyl, propyl, isopropyl, ethoxyethyl, ethoxymethyl, pivaloyloxymethyl, acetoxymethyl, 1-acetoxyethyl, 1-n-propionyloxyethyl, 1-ethoxycarbonyloxyethyl and 5-methyl-1,3-dioxol-2-on-4-ylmethyl.

The cromoglycic acid derivatives (I) are preferably in the form of acid addition salts (nontoxic salts) at the amino acid residue thereof. Any of those acids which are capable of forming salts with the amino acid residue moiety and are pharmaceutically acceptable may be used as the salt for forming such acid addition salts without any particular limitations. Examples of such acid are inorganic acids, such as hydrochloric acid, sulfuric acid, phosphoric acid and nitric acid, and organic acids, such as oxalic acid, fumaric acid, maleic acid, citric acid, tartaric acid, methanesulfonic acid and toluenesulfonic acid. Conversion to such salts results in further improvement in absorbability through the digestive tract and facilitation of dosage form preparation.

The cromoglycic acid derivatives (I) according to the present invention can be produced in the following manner, for instance:

A compound (III) of the general formula (III):

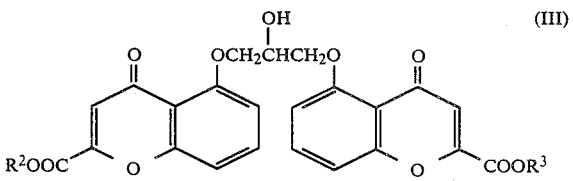

wherein $R^2$ and $R^3$ are as previously defined, is reacted with a compound (IV) of the general formula (IV):

$$R^1OH \qquad (IV)$$

wherein $R^1$ is as defined above.

The compound (IV) is subjected to the above reaction either in the form of a free carboxylic acid or in the form of a reactive derivative thereof. Thus, said compound is subjected to the acylation in the form of a free acid or a salt thereof with sodium, potassium, calcium, triethylamine, pyridine or the like, or in the form of a reactive derivative thereof, such as an acid halide (acid chloride, acid bromide, etc.), an acid anhydride, a mixed acid anhydride [with a substituted phosphoric acid (dialkylphosphoric acid, etc.), an alkylcarbonic acid (monoethylcarbonic acid, etc.)], an active amide (amide with imidazole or the like) or an ester (cyanomethyl ester, 4-nitrophenyl ester, or the like).

When the compound (IV) is used in the form of a free acid, it is preferable to use an appropriate condensing agent. Usable as the condensing agent are, for example, dehydrating agents, such as N,N'-substituted carbodiimides (e.g. N,N'-dicyclohexylcarbodiimide) and azolide compounds (e.g. N,N-carbonyldiimidazole and N,N'-thionyldiimidazole). When these condensing agents are used, the reaction presumably proceeds via a reactive derivative of the carboxylic acid. In carrying out this reaction, the use of a base, such as 4-dimethylaminopyridine, as a catalyst is preferable.

When the amino group in the compound (IV) to be subjected to the above reaction is a primary or secondary one, this amino group should preferably be protected by an amino-protecting group, such as 2,2,2-trichloroethoxycarbonyl, 2-methylsulfonylethyloxycarbonyl, t-butoxycarbonyl, chloroacetyl or trityl.

This reaction is generally carried out in an inert solvent. As specific examples of the solvent, there may be mentioned water, organic solvents, such as acetone, dioxane, acetonitrile, chloroform, benzene, methylene chloride, ethylene chloride, tetrahydrofuran, ethyl acetate, N,N-dimethylformamide and pyridine, and mixtures of these.

The compound (III) can be produced from cromoglycic acid (II), which is a known compound, in the following manner:

A cromoglycic acid salt (salt with an alkali metal or alkaline earth metal, such as lithium, sodium, potassium or cesium, or salt with an organic amine, such as trimethylamine, triethylamine or pyridine) is reacted with a compound (V) of the general formula $$R-X \qquad (V)$$

wherein R is the same as $R^2$ or $R^3$ and X is a group reactive with the carbonyl group, in a polar solvent, such as N,N-dimethylformamide, N,N-dimethylacetamide, dimethyl sulfoxide or hexamethylphosphoramide, at room temperature to 100° C.

In place of said cromoglycic acid salt, cromoglycic acid may be subjected to the reaction in the presence of an alkali metal salt of carbonic acid (e.g. sodium hydrogen carbonate, potassium carbonate), an alkaline earth metal salt of carbonic acid (e.g. cesium carbonate) or an alkali metal or alkaline earth metal salt of a lower alkanoic acid (e.g. acetic acid).

This reaction may also be carried out in a bilayer system composed of an organic solvent, such as chloroform or methylene chloride, and water in the presence of a catalitic amount of a quarternary ammonium chloride (e.g. a phase transfer catalyst such as benzyltributylammonium chloride).

As the group reactive with the carboxyl group as represented by X in general formula (V), there may be mentioned halogen atoms, such as Cl, Br and I, methyl- and tolyl-sulfonate, and so on.

When the cromoglycic acid derivatives (I) obtained are in the free base form, they may be converted to nontoxic acid addition salts by a per se known means.

The thus-produced cromoglycic acid derivatives (I) or nontoxic salts thereof are formulated into pharmaceutical compositions for use, for example, as antiallergic drugs for oral administration by mixing therapeutically effective amounts of said compounds with pharmaceutically acceptable additives, such as excipients.

Examples of the excipients are starch, lactose, sucrose, calcium carbonate and calcium phosphate.

Meanwhile, it is preferable to further add an organic acid to pharmaceutical compositions like said antiallergic drugs for oral administration. Thus the solubility of the cromoglycic acid derivatives in the digestive tract is increased and their absorbability into the blood after oral administration is facilitated. Any of those organic acids which are pharmaceutically acceptable can be used without any particular limitation and, as preferred examples, there may be mentioned organic carbocylic acids such as maleic acid, fumaric acid, tartaric acid, citric acid, succinic acid, malic acid, oxalic acid, mandelic acid, malonic acid and benzoic acid. Such organic acids are added generally in an amount of 0.01–20 moles, preferably in an amount of 1–10 moles, per mole of cromoglycic acid derivative (I).

Other additives may further be incorporated in said pharmaceutical compositions, as desired. Preferred examples of the additives are, for example, binders (e.g. starch, gum arabic, carboxymethylcellulose, hydroxypropylcellulose, crystalline cellulose, etc.), lubricants (e.g. magnesium stearate, talc, etc.) and disintegrants (e.g. carboxymethylcellulose calcium, talc, etc.). After admixing of the ingredients, the mixture can be made up into dosage forms suited for oral administration, such as capsules, tablets, fine granules, granules and dry syrups, by a per se known means.

The cromoglycic acid derivatives (I) and nontoxic salts thereof according to the present invention are used, in the same manner as cromoglycic acid (II), as oral antiallergic agents for treating allergic diseases, such as bronchial asthma, allergic rhinitis, irritable pharyngolarynx, spring catarrh and chronic allergic conjunctivitis.

In administering them orally, a daily dose is desirably administered orally in a single or divided doses. The daily dose may vary depending on the state of disease, age, body weight and other factors. For their use as oral antiallergic agents in human adults, 1–500 mg can be administered in 1–4 divided doses per day.

The following working examples and test examples illustrate the present invention in further detail but are by no means limitative of the invention.

The following abbreviations are used hereinafter:
DSCG: Disodium cromoglycate
DMF: Dimethylformamide
DCC: N,N'-Dicyclohexylcarbodiimide
DMSO: Dimethyl sulfoxide
BOC: t-Butoxycarbonyl

EXAMPLE 1

Synthesis of diethyl L-lysylcromoglycate dihydrochloride (1) Diethyl cromoglycate (524 mg), 520 mg of di-BOC-L-lysine and 61 mg of dimethylaminopyridine are added to 10 ml of methylene chloride. DCC (310 mg) is added at 0° C. and the mixture is stirred at that temperature for 30 minutes, and then stirred at room temperature for 6 hours. After the precipitate urea compound is filtered off, the filtrate is concentrated and purified by silica gel column chromatography to give 580 mg of diethyl di-BOC-L-lysylcromoglycate (yield 68%).

IR (KBr, cm$^{-1}$) 1740, 1710, 1690, 1655

NMR (CDCl$_3$, δ ppm): 1.41 (18H, s, —C(CH$_3$)$_3$); 1.41 (6H, t, J=7 Hz, —CH$_2$CH$_3$); 1.4~2.1 (6H, m, —(CH$_2$)$_3$—); 2.8~3.3 (2H, m, —CH$_2$NH—); 3.9~4.4 (1H, m,

4.43 ( 4H, q, J=7 Hz, —CH$_2$CH$_3$); 4.3~4.8 (4H, m,

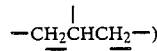

4.7~5.5 (2H, m, —NH—); 5.4~5.9 (1H, m

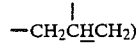

6.87 (2H, s, —H in position 3 of chromone nucleus); 6.8~7.4 (4H, m, —H in position 6 and in position 8 of chromone nucleus); 7.58 (2H, t, J=9 Hz, —H in position 7 of chromone nucleus);

(2) The compound obtained in (1) (470 mg) is dissolved in 1.1 ml of formic acid. With ice cooling, 2.8 ml of 1.4M hydrochloric acid solution in dioxane is added. The mixture is stirred at room temperature for 30 minutes. The reaction mixture is poured into isopropyl ether and the precipitate is collected by filtration to give 351 mg of diethyl L-lysylcromoglycate dihydrochloride (yield 88%).

IR (KBr, cm$^{-1}$) 1740

NMR (DMSO-d$_6$, δ ppm): 1.34 (6H, t, J=7 Hz, —CH$_2$CH$_3$); 1.4~2.2 (6H, m, —(CH$_2$)$_3$—); 2.3~3.0 (2H, m, —CH$_2$NH$_3$$^+$); 3.7~4.2 (1H, m,

4.36 (4H, q, J=7 Hz, —CH$_2$CH$_3$); 4.3~4.9 (4H, m,

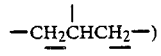

5.4~5.9 (1H, m,

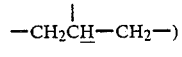

6.72, 6.74 (2H, s, —H in position 3 of chromone nucleus); 7.12, 7.19 (4H, d, J=9 Hz, —H in position 6 and in position 8 of chromone nucleus); 7.74 (2H, t, J=9 Hz, —H in position 7 of chromone nucleus); 7.5~9.0 (6H, br, —NH$_3^+$)

EXAMPLE 2

Synthesis of diethyl glycylcromoglycate hydrochloride

Using BOC-glycine and proceeding in the same manner as in Example 1, there is obtained diethyl glycylcromoglycate hydrochloirde.

IR (KBr, cm$^{-1}$) 1740, 1650

NMR (DMSO-d$_6$, δ ppm): 1.34 (6H, t, J=7 Hz, —CH$_2$CH$_3$); 3.84 (2H, br.s, —CH$_2$NH$_3^+$); 4.38 (4H, q, J=7 Hz, —CH$_2$CH$_3$); 4.49~4.87 (4H, m,

5.49–5.89 (1H, m,

6.69 (2H, s, —H in position 3 of chromone nucleus); 6.95~7.38 (4H, m, —H in position 6 and in position 8 of chromone nucleus); 7.72 (2H, t, J=9 Hz, —H in position 7 of chromone nucleus); 8.2~9.5 (3H, br, —NH$_3^+$)

EXAMPLE 3

Synthesis of dimethyl L-alanylcromoglycate hydrochloride

Using dimethyl cromoglycate and BOC-L-alanine and proceeding in the same manner as in Example 1, there is obtained dimethyl L-alanylcromoglycate hydrochloride.

IR (nujol, cm$^{-1}$) 1745

NMR (DMSO-d$_6$, δ ppm): 1.43 (3H, d, J=8 Hz,

3.92 (6H, s, —OCH$_3$); 4.10 (1H, q, J=8 Hz,

4.4~4.8 (4H, br,

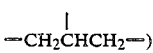

5.4~5.8 (1H, br,

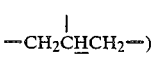

6.70, 6.74 (2H, s, —H in position 3 of chromone nucleus); 7.08, 7.20 (4H, d, J=9 Hz, —H in position 6 and in position 8 of chromone nucleus); 7.74 (2H, t, J=9 Hz, —H in position of 7 of chromone nucleus); 8.3–8.9 (3H, br, —NH$_3^+$)

EXAMPLE 4

Synthesis of diethyl L-alanylcromoglycate hydrochloride

Using BOC-L-alanine and proceeding in the same manner as in Example 1, there is obtained diethyl L-alanylcromoglycate hydrochloride.

IR (KBr, cm$^{-1}$) 1740

NMR (DMSO-d$_6$, δ ppm): 1.34 (6H, t, J=7 Hz, —CH$_2$CH$_3$); 1.46 (3H, d, J=8 Hz,

3.9~4.5 (1H, m,

4.36 (4H, q, J=7 Hz, —CH$_2$C$_3$); 4.3~4.8 (4H, m,

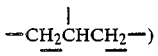

5.3~5.9 (1H, m,

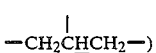

6.69, 6.71 (2H, s, —H in position 3 of chromone nucleus); 7.06, 7.21 (4H, d, J=9 Hz, —H in position 6 and in position 8of chromone nucleus); 7.73 (2H, t J=9 Hz, —H in position 7 of chromone nucleus); 8.0~9.0 (3H, br, —NH$_3^+$)

EXAMPLE 5

Synthesis of diethyl β-alanylcromoglycate hydrochloride

Using BOC-β-alanine and proceeding in the same manner as in Example 1, there is obtained diethyl β-alanylcromoglycate hydrochloride.

IR (KBr, cm$^{-1}$) 1740, 1650

NMR (DMSO-d$_6$, δ ppm): 1.34 (6H, t, J=7 Hz, —CH$_2$CH$_3$—); 2.7~3.2 (4H, m, —CH$_2$CH$_2$—); 4.37 (4H, q, J=7 Hz, —CH$_2$CH$_3$); 4.52 (4H, br.s,

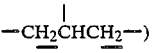

5.4~5.75 (1H, br,

6.70 (2H, s, —H in position 3 of chromone nucleus); 6.9~7.35 (4H, m, —H in position 6 and in position 8 of chromone nucleus); 7.72 (2H, t, J=9 Hz, —H in position 7 of chromone nucleus); 7.9~8.4 (3H, br, —NH$_3^+$).

EXAMPLE 6

Synthesis of diethyl N-glycylglycylcromoglycate hydrochloride

Using N-(BOC-glycyl)glycine and proceeding in the same manner as in Example 1, there is obtained diethyl N-glycylglycylcromoglycate hydrochloride.

IR (KBr, cm$^{-1}$) 1740, 1690, 1650

NMR (DMSO-d$_6$, δ ppm): 1.34 (6H, t, J=7 Hz, —CH$_2$CH$_3$); 3.5~5.0 (12H, m,

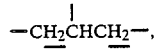

—CH$_2$CH$_3$, —CH$_2$NHCOCH$_2$—); 5.2~5.9 (1H, m,

6.69 (2H, s, —H in position 3 of chromone nucleus); 7.08, 7.17 (4H, d, J=9 Hz, —H in position 6 and in position 8 of chromone nucleus); 7.72 (2H, t, J=9 Hz, —H in position 7 of chromone nucleus); 7.7~8.7 (3H, m, —NH$_3{}^+$); 8.5~9.2 (1H, m, —NH—);

EXAMPLE 7

Synthesis of diethyl N-(L-alanyl)glycylcromoglycate hydrochloride

Using N-(BOC-L-alanyl)glycine and proceeding in the same manner as in Example 1, there is obtained diethyl N-(L-alanyl)glycylcromoglycate hydrochloride.

IR (KBr, cm$^{-1}$) 1740, 1650

NMR (DMSO-d$_6$, δ ppm): 1.34 (6H, t J=7 Hz, —CH$_2$CH$_3$); 1.40 (3H, d, J=8 Hz,

3.6~4.3 (3H, m, —COCH$_2$NH—,

4.38 (4H, q, J=7 Hz, —CH$_2$CH$_3$); 4.2~4.8 (4H, m,

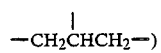

5.2~5.8 (1H, m,

6.68 (2H, s, —H in position 3 of chromone nucleus); 7.06, 7.18 (4H, d, J=9 Hz, —H in position 6 and in position 8 of chromone nucleus); 7.71 (2H, t, J=9 Hz, —H in position 7 of chromone nucleus); 7.9, 8.6 (3H, m, —NH$_3{}^+$); 8.6~9.1 (1H, m, —NH—)

EXAMPLE 8

Synthesis of diethyl N-(L-leucyl)glycylcromoglycate hydrochloride

Using N-(BOC-L-leucyl)glycine and proceeding in the same manner as in Example 1, there is obtained diethyl N-(L-leucyl)glycylcromoglycate hydrochloride.

IR (KBr, cm$^{-1}$) 1740, 1655

NMR (DMSO-d$_6$, δ ppm): 0.89 (6H, d, J=5 Hz, CH(CH$_3$)$_2$); 1.35 (6H, t, J=7 Hz, —CH$_2$CH$_3$); 1.3~2.1 (3H, m,

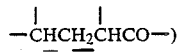

3.6~4.3 (3H, m, —NHCH$_2$CO—,

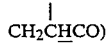

4.38 (4H, q, J=7 Hz, —CH$_2$CH$_3$); 4.3~4.9 (4H, m,

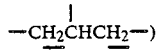

5.3~5.8 (1H, br,

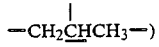

6.68 (2H, s, —H in position 6 of chromone nucleus); 7.06, 7.17 (4H, d, J=9 Hz, —H in position 3 and in position 8 of chromone nucleus); 7.71 (2H, t, J=9 Hz, —H in position 7 of chromone nucleus); 7.9~8.6 (3H, m, —NH$_3{}^+$); 8.7~9.2 (1H, m, —NH—);

EXAMPLE 9

Synthesis of diethyl L-valylcromoglycate hydrochloride

Using BOC-L-valine and proceeding in the same manner as in Example 1, there is obtained diethyl L-valylcromoglycate hydrochloride.

IR (KBr, cm$^{-1}$) 1735, 1650:

NMR (DMSO-d$_6$, δ ppm): 0.92 (6H, d, J=7 Hz, —CH(CH$_3$)$_2$); 1.34 (6H, t J=7 Hz, —CH$_2$CH$_3$); 1.81~2.31 (1H, m, —CH(CH$_3$)$_2$); 3.81~4.05 (1H, m,

4.38 (4H, q, J=7 Hz, —CH$_2$CH$_3$); 4.48~4.73 (4H, m,

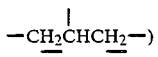

5.5~5.86 (1H, m,

6.71~7.91 (8H, m, —H in position 3, in position 6, in position 7 and in position 8 of chromone nucleus); 8.32~8.83 (3H, br, —NH₃⁺);

EXAMPLE 10

Synthesis of diethyl L-leucylcromoglycate hydrochloride

Using BOC-L-leucine and proceeding in the same manner as in Example 1, there is obtained diethyl L-leucylcromoglycate hydrochloride.

IR (KBr, cm⁻¹) 1740, 1650:

NMR (DMSO-d₆, δ ppm): 0.76 (6H, m, —CH(CH₃)₂); 1.34 (6H, t, J=7 Hz, —CH₂CH₃); 1.51~1.96 (3H, m, —CH₂CH(CH₃)₂); 3.93~4.04 (1H, m,

4.39 (4H, q, J=7 Hz, —CH₂CH₃); 4.49~4.83 (4H, m,

5.44~5.83 (1H, m,

6.72~7.92 (8H, m, —H in position 3, in position 6, in position 7 and in position 8 of chromone nucleus); 8.27~9.03 (3H, br, —NH₃⁺)

EXAMPLE 11

Synthesis of di(2-ethoxyethyl) L-lysylcromoglycate dihydrochloride (1) To a mixture of 3 ml of triethylamine and 20 ml of DMF, there are added 3 ml of 2-ethoxyethyl bromide and 4 g of DSCG and the mixture is stirred at 90° C. for 3 hours. To the reaction mixture, there are added 200 ml of water and 50 ml of ethyl acetate. The organic layer is separated, washed with aqueous sodium bicarbonate solution and aqueous sodium chloride solution, and dried over sodium sulfate. After removal of the solvent by distillation, the residue is purified by silica gel column chromatography to give 2.6 g of di(2-ethoxyethyl) cromoglycate (yield 50%).

IR (KBr, cm⁻¹) 3400, 1745, 1730, 1650:

NMR (CDCl₃, δ ppm): 1.23 (6H, t, J=7 Hz, —CH₂CH₃); 2.6~3.5 (1H, br, —OH); 3.57 (4H, q, J=7 Hz, —CH₂CH₃); 3.74 (4H, t, J=5 Hz, —CO₂CH₂CH₂—); 4.1~4.8 (5H, m,

4.50 (4H, t, J=5 Hz, —CO₂CH₂—); 6.8~7.4 (6H, —H in position 3, in position 6 and in position 8 of chromone nucleus); 7.58 (2H, t, J=9 Hz, —H in position 7 of chromone nucleus)

(2) Using diBOC-L-lysine and proceeding in the same manner as in Example 1, there is obtained di(2-ethoxyethyl) L-lysylcromoglycate dihydrochloride.

IR (KBr, cm⁻¹) 3450, 1745:

NMR (DMSO-d₆, δ ppm): 1.14 (6H, t, J=7 Hz, —CH₂_LL_ CH₃); 1.2~2.1 (6H, m, —(CH₂)₃—); 2.4~2.9 (2H, m, —CH₂NH₃⁺); 3.52 (4H, q, J=7 Hz, —CH₂CH₃—); 3.4~4.0 (4H, m, —CH₂CH₂O—); 3.8~4.2 (1H, m,

4.0~5.0 (8H, m,

—CO₂CH₂—); 5.4~5.9 (1H, m,

6.73~6.75 (2H, s, —H in position 3 of chromone nucleus); 6.9~7.4 (4H, m, —H in position 6 and in position 8 of chromone nucleus); 7.76 (2H, t, J=9 Hz, —H in position 7 of chromone nucleus); 7.4~9.5 (6H, m, —NH₃⁺)

EXAMPLE 12

Synthesis of di(2-ethoxyethyl) L-alanylcromoglycate hydrochloride

Proceeding in the same manner as in Example 11, there is obtained di(2-ethoxyethyl) L-alanylcromoglycate hydrochloride.

IR (KBr, cm⁻¹) 1745, 1655:

NMR (DMSO-d₆, δ ppm): 1.14 (6H, t, J=7 Hz, —CH₂CH₃); 1.43 (3H, d, J=8 Hz,

3.52 (4H, q, J=7 Hz, —CH₂CH₃); 3.5~4.0 (4H, m, —CH₂CH₂O); 4.05 (1H, m,

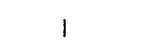

4.1~4.9 (8H, m.,

—CO₂CH₂—); 5.3~5.9 (1H, m,

—CH₂CHCH₂—)

6.7~6.73 (2H, s, —H in position 3 of chromone nucleus); 6.9~7.4 (4H, m, —H in position 6 and in position 8 of chromone nucleus); 7.75 (2H, t, J=9 Hz, —H in position 7 of chromone nucleus); 8.0~9.0 (3H, br, —NH$_3^+$)

EXAMPLE 13

Synthesis of di(2-ethoxyethyl) N-(L-alanyl)glycylcromoglycate hydrochloride

Using N-(BOC-L-alanyl)glycine and proceeding in the same manner as in Example 11, there is obtained di(2-ethoxyethyl) N-(L-alanyl)glycylcromoglycate hydrochloride.

IR (KBr, cm$^{-1}$) 1735, 1720, 1650:

NMR (DMSO-d$_6$, δ ppm): 1.13 (6H, t, J=7 Hz, —CH$_2$CH$_3$); 1.37 (3H, d, J=8 Hz,

3.5 (4H, q, J=7 Hz, —CH$_2$CH$_3$); 3.5~3.9 (4H, m, —CH$_2$CH$_2$O—); 3.8~4.2 (3H, m,

—CH$_2$NH); 4.1~4.9 (8H, m,

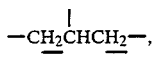

—CO$_2$CH$_2$—); 5.3~5.8 (1H, m,

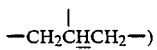

6.7 (2H, s, —H in position 3 of chromone nucleus); 7.08, 7.17 (4H, d, J=9 Hz, —H in position 6 and in position 8 of chromone nucleus); 7.72 (2H, t, J=9 Hz, —H in position 7 of chromone nucleus); 7.5~8.5 (3H, br, —NH$_3^+$); 8.6~9.1 (1H, br, —NHCO—)

EXAMPLE 14

Synthesis of di(pivaloyloxymethyl) L-lysylcromoglycate dihydrochloride (1) After Di(pivaloyloxymethyl) cromoglycate (500 mg) is dissolved in 4 ml of methylene chloride, 370 mg of diBOC-L-lysine is added, and then 14 mg of dimethylaminopyridine is added and furthermore 1.8 ml of 1M DCC solution in methylene chloride is added dropwise at 0° C. After 4 hours of stirring, the precipitate urea compound is filtered off and the filtrate residue is purified by silica gel column chromatography to give 710 mg of di(pivaloyloxymethyl) diBOC-L-lysylcromoglycate (yield 97%).

IR (nujol, cm$^{-1}$) 1755, 1710, 1655:

NMR (CDCl$_3$, δ ppm): 1.36 (18H, s, (CH$_3$)$_3$CCO); 1.41, 1.43 (18H, s, BOC); 1.6~2.1 ( 4.0~4.4 (1H, m,

4.60 (4H, br,

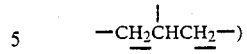

5.1~5.4 (2H, br, —NH—); 5.5~5.8 (1H, m,

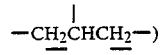

;

5.98 (4H, s, —OCH$_2$O—); 6.90 (2H, s, —H in position 3 of chromone nucleus); 6.98, 7.12 (4H, d, J=9 Hz, —H in position 6 and in position 8 of chromone nucleus); 7.62 (2H, t, J=9 Hz, —H in position 7 of chromone nucleus)

(2) The compound obtained in 1) (400 mg) is dissolved in 0.8 ml of formic acid, then 2 ml of 1.4M hydrogen chloride solution in dioxane is added, and the mixture is stirred at room temperature for 5 minutes. By adding isopropyl ether, there is obtained 300 mg of di(pivaloyloxymethyl) L-lysylcromoglycate dihydrochloride (yield 86%).

IR (nujol, cm$^{-1}$) 1760, 1660:

NMR (DMSO-d$_6$, δ ppm): 1.20 (18H, s, —C(CH$_3$)$_3$); 1.4~2.1 (6H, br, —(CH$_2$)$_3$—); 2.4~3.0 (2H, m, —CH$_2$NH$_3^+$); 3.8~4.2 (1H, m,

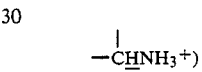

4.4~4.8 (4H, m,

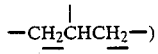

5.5~5.8 (1H, m,

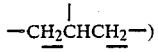

5.98 (4H, s, —OCH$_2$O—); 6.77, 6.78 (2H, s, —H in position 3 of chromone nucleus); 7.10, 7.20 (4H, d, J=9 Hz, —H in position 6 and in position 8 of chromone nucleus); 7.78 (2H, t, J=9 Hz, —H in position 7 of chromone nucleus); 8.0~9.2 (6H, br, —NH$_3^+$)

EXAMPLE 15

Synthesis of di(pivaloyloxymethyl) L-alanylcromoglycate hydrochloride

Using BOC-L-alanine and proceeding in the same manner as in Example 14, there is obtained di(pivaloyloxymethyl) L-alanylcromoglycate hydrochloride.

IR (nujol, cm$^{-1}$) 1760, 1660:

NMR (DMSO-d$_6$, δ ppm): 1.19 (18H, s, —C(CH$_3$)$_3$); 1.43 (3H, d, J=8 Hz,

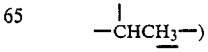

4.0~4.8 (5H, m,

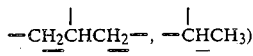

5.3~5.8 (1H, m,

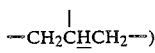

5.96 (4H, s, —OCH$_2$O—); 6.73 (2H, s, —H in position 3 of chromone 7.10, 7.25 (4H, d, J=9 Hz, —H in position 6 and in position 8 of chromone nucleus); 7.74 (2H, t, J=9 Hz, —H in position 7 of chromone nucleus); 8.2~8.6 (3H, br, —NH$_3^+$)

EXAMPLE 16

Synthesis of di(acetoxymethyl) β-alanylcromoglycate hydrochloride

Using di(acetoxymethyl) cromolgycate and BOC-β-alanine and proceeding in the same manner as in Example 14, there is obtained di(acetoxymethyl) β-alanylcromoglycate hydrochloride.

IR (KBr, cm$^{-1}$) 1760, 1660:

NMR (DMSO-d$_6$, δ ppm): 2.13 (6H, s, —CH$_3$); 2.6~3.3 (4H, m, —CH$_2$CH$_2$—); 4.2~4.9 (4H, m,

5.3~5.9 (1H, m,

5.92 (4H, s, —OCH$_2$O—); 6.72 (2H, s, —H in position 3 of chromone nucleus); 7.07, 7.20 (4H, d, J=9 Hz, —H in position 6 and in position 8 of chromone nucleus); 7.73 (2H, t, J=9 Hz, —H in position 7 of chromone nucleus); 7.6~8.5 (3H, br, —NH$_3^+$)

EXAMPLE 17

Synthesis of di(1-acetoxyethyl) N-(glycyl)glycylcromoglycate hydrochloride (1) DSCG(6.1 g) is dissolved in 96 ml of water. After Chloroform (96 ml) and 7.5 g of benzyltri-n-butylammonium chloride are added, 4 g of 1-bromoethyl acetate is added dropwise over 15 minutes, while the pH is maintained at 6 with NaHCO$_3$. After 45 hours of stirring, the chloroform layer is separated and dried over sodium sulfate. The solvent is distilled off and the residue is purified by silica gel column chromatography to give 4.4 g of di(1-acetoxyethyl) cromoglycate (yield 58%).

IR (KBr, cm$^1$) 1760, 1650:

NMR (CDCl$_3$, δ ppm): 1.63 (6H, d, J=9 Hz,

2.12 (6H, s, —COCH$_3$) 3.96 (1H, br, —OH) 4.45 (5H, m,

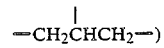

6.8~7.35 (10H, m, —H in position 3, in position 6 and in position 8 of chromone nucleus,

7.6 (2H, t, J=9 Hz, —H in position 7 of chromone nucleus)

(2) After the compound obtained in 1) (780 mg) is dissolved in 8 ml of methylene chloride, 396 mg of N-(BOC-glycyl)glycine, 74 mg of dimethylaminpyridine and 352 mg of DCC are added, and the mixture is stirred at 0° C. for 17 hours. The precipitated urea compound is filtered off, and the filtrate is washed with aqueous citric acid solution and dried over sodium sulfate. After removal of the solvent by distillation, the residue is purified by silica gel column chromatography to give 669 mg of di(1-acetoxyethyl) N-(BOC-glycyl)-glycylcromoglycate (yield 64%).

IR (KBr, cm$^{-1}$) 1760, 1715, 1650:

NMR (CDCl$_3$, δ ppm): 1.44 (9H, s, —C(CH$_3$)$_3$); 1.63 (6H, d, J=6 Hz,

2.12 (6H, s, —COCH$_3$); 3.8~4.3 (4H, m, —CH$_2$NHCOCH$_2$—); 4.4~4.8 (4H, m,

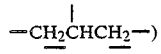

5.2~5.9 (3H, m, —NHCO,

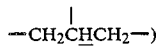

6.8~7.3 (10H, m,

—H in position 3, in position 6 and in position 8 of chromone nucleus); 7.59 (2H, t, J=9 Hz, —H in position 7 of chromone nucleus)

(3) The compound obtained in 2) (600 mg) is dissolved in 1.2 ml of formic acid and, with ice cooling, 3.6 ml of 1.3M hydrogen chloride solution in dioxane is added. The mixture is stirred at room temperature for 30 minutes. The reaction mixture is poured into isopropyl ether and the resultant precipitate is collected by filtration and dried to give 492 mg of di(1-acetoxyethyl) N-(glycyl)glycylcromoglycate hydrochloride (yield 89%).

IR (KBr, cm$^{-1}$) 1760, 1690, 1655:

NMR (DMSO-d$_6$, δ ppm): 1.57 (6H, d, J=9 Hz, 2.10 (6H, s, —COCH₃); 3.7~4.3 (4H, m, —CH₂NH-COCH₂—); 4.2~4.9 (4H, m,

—CH₂CH̲CH₂—)

5.2~5.8 (1H, m,

—CH₂C̲HCH₂—)

6.73 (2H, m, —H in position 3 of chromone nucleus); 6.7~7.4 (6H, m, —H in position 6 and in position 8 of chromone nucleus,

—C̲HCH₃)

7.72 (2H, t, J=9 Hz, —H in position 7 of chromone nucleus); 8.6 (3H, m, —NH₃⁺); 8.6~9.0 (1H, m, —NH-CO—);

EXAMPLE 18

Synthesis of di(1-acetoxyethyl) N-(L-alanyl)glycylcromoglycate hydrochloride

Using N-(BOC-L-alanyl)glycine and proceeding in the same manner as in Example 17, there is obtained di(1-acetoxyethyl) N-(L-alanyl)glycylcromoglycate hydrochloride.

IR (KBr, cm⁻¹) 1750, 1650:
NMR (DMSO-d₆, δ ppm): 1.36 (3H, d, J=8 Hz,

CH₃C̲HCO—)
;
1.58 (6H, d, J=6 Hz,

CH₃C̲HO—)

2.10 (6H, s, CH₃CO—); 3.8~4.2 (3H, m, —CH₂NH—,

—C̲HCH₃)

4.2~4.8 (4H, m,

—CH₂C̲HCH₂—)

5.3~5.8 (1H, m,

—CH₂C̲HCH₂—)

6.72 (2H, s, —H in position 3 of chromone nucleus); 6.8~7.35 (6H, m, —H in position 6 and in position 8 of chromone nucleus,

CH₃C̲HO—)

7.72 (2H, t, J=9 Hz, —H in position 7 of chromone nucleus); 8.0~8.4 (3H, br, —NH₃⁺); 8.7~9.1 (1H, br, —NHCO—);

EXAMPLE 19

Synthesis of di(1-acetoxyethyl) L-alanylcromoglycate hydrochloride

Using BOC-L-alanine and proceeding in the same manner as in Example 17, there is obtained di(1-acetoxyethyl) L-alanylcromoglycate hydrochloride.

IR (KBr, cm⁻¹) 1760, 1655:
NMR (DMSO-d₆, δ ppm): 1.42 (3H, d, J=8 Hz,

—COC̲HCH₃)

1.57 (6H, d, J=6 Hz,

CH₃C̲HO—)

2.09 (6H, s, CH₃CO—) 4.04~4.17 (1H, m,

—COC̲HCH₃—)

4.28~4.8 (4H, m,

—CH₂C̲HCH₂—)

5.44~5.82 (1H, m,

—CH₂C̲HCH₂—)

6.76~7.92 (10H, m, —H in position 3, in position 6, in position 7 and in position 8 of chromone nucleus,

CH₃C̲HO—)

8.0~8.7 (3H, m, —NH₃⁺);

EXAMPLE 20

Synthesis of di(1-acetoxyethyl) β-alanylcromoglycate hydrochloride

Using BOC-β-alanine and proceeding in the same manner as in Example 17, there is obtained di(1-acetoxyethyl) β-alanylcromoglycate hydrochloride.
IR (KBr, cm$^{-1}$) 1760, 1655:
NMR (DMSO-d$_6$, δ ppm): 1.60 (6H, d, J=6 Hz,

2.12 (6H, s, —COCH$_3$); 2.7~3.35 (4H, m, —CH$_2$CH$_2$—); 4.3~4.85 (4H, m,

5.4~5.8 (1H, m,

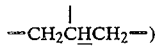

6.74 (2H, s, —H in position 3 of chromone nucleus); 6.7~7.4 (6H, m. —H in position 6 and in position 8 of chromone nucleus,

7.23 (2H, t, J=9 Hz, —H in position 7 of chromone nucleus); 7.9~8.4 (3H, br, —NH$_3$+)

EXAMPLE 21

Synthesis of di(1-acetoxyethyl) L-lysylcromoglycate dihydrochloride

Using di-BOC-L-lysine and proceeding in the same manner as in Example 17, there is obtained di(1-acetoxyethyl) L-lysylcromoglycate dihydrochloride.
IR (KBr, cm$^{-1}$) 1770, 1660:
NMR (DMSO-d$_6$, δ ppm): 1.58 (6H, d, J=6 Hz,

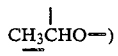

1.2~2.0 (6H, m, —(CH$_2$)$_3$—); 2.10 (6H, s, CH$_3$CO—); 2.4~2.8 (2H, m, —CH$_2$NH$_3$+); 3.9~4.2 (1H, m,

4.43~4.85 (4H, m,

5.48~5.91 (1H, m,

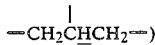

6.75~7.45 (8H, m, —H in position 3, in position 6 and in position 8 of chromone nucleus,

7.75 (2H, t, J=9 Hz, —H in position 7 of chromone nucleus) 7.5~9.1 (6H, br, —NH$_3$+)

EXAMPLE 22

Synthesis of di(5-methyl-2-on-1,3-dioxol-4-ylmethyl) L-α-aspartylcromoglycate dihydrochloride (1) After DSCG(1 g) is dissolved in 40 ml of DMF, 0.91 g of 4-bromomethyl-5-methyl-1,3-dioxol-2-one is added, and the mixture is stirred at 40° C. for 2 hours. Water (400 ml) is added and the mixture is extracted with methylene chloride. The extract is washed with water and dried, and the solvent is distilled off to give 1.0 g of di(5-methyl-2-on-1,3-dioxol-4-ylmethyl) cromoglycate (yield 80%).
IR (nujol, cm$^{-1}$)1825, 1750:
NMR (DMSO-d$_6$, δ ppm): 2.22 (6H, s, dioxole—CH$_3$); 4.32 (5H, s,

5.26 (6H, s, dioxole—CH$_2$—, —OH); 6.73 (2H, s, —H in position 3 of chromone nucleus); 6.87-7.33 (4H, m, —H in position 6 and in position 8 of chromone nucleus); 7.71 (2H, t, J=9 Hz, —H in position 7 of chromone nucleus);

(2) The compound obtained in (1) (1.0 g) is dissolved in 10 ml of methylene chloride. To the solution are added 531 mg of β-t-butyl BOC-L-asparatate and 88 mg of dimethylaminopyridine and, after further addition of 417 mg of DCC, the mixture is stirred at 0° C. for 5 hours. After the precipitated urea compound is filtered off, the solvent is distilled off and ethyl acetate is added to the residue. The resultant solution is washed with aqueous citric acid solution and then with aqueous sodium chloride solution and dried over sodium sulfate. After removal of the solvent by distillation, the residue is purified by silica gel column chromatography to give 625 mg of di(5-methyl-2-on-1,3-dioxol-4-ylmethyl) N-BOC-β-t-butyl-L-aspartylcromoglycate (yield 45%).
IR (KBr, cm$^{-1}$) 1820, 1745, 1720, 1655:
NMR (CDCl$_3$, δ ppm): 1.36, 1.42 (18H, s, —C(CH$_3$)$_3$); 1.5~1.8 (1H, br, —NH—) 2.24 (6H, s, dioxole—CH); 2.7~3.0 (2H, d, J=5 Hz, —CH$_2$CO$_2$—); 4.3~4.9 (4H, m,

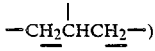

5.10 (4H, s, dioxole—CH$_2$—); 5.2~6.0 (2H, m 6.85 (2H, s, —H in position 3 of chromone nucleus); 6.8~7.3 (4H, m, —H in position 6 and in position 8 of chromone nucleus); 7.57 (2H, t, J=9 Hz, —H in position 7 of chromone nucleus)

(3) The compound obtained in (2) (377 mg) is dissolved in 0.8 ml of formic acid and, with ice cooling, 2 ml of 1.4M hydrogen chloride solution in dioxane is added. The mixture is stirred at room temperature for 20 hours. The reaction mixture is poured into isopropyl ether to give 379 mg of di(5-methyl-2-on-1,3-dioxol-4-ylmethyl) L-α-aspartylcromoglycate hydrochloride (yield 95%).

IR (KBr, cm$^{-1}$) 1820, 1750, 1655:

NMR (DMSO-d$_6$, δ ppm): 2.22 (6H, s, dioxole—CH$_3$); 2.6~3.3 (2H, m, —CH$_2$CO$_2$—); 4.1~4.6 (1H, m,

4.2~4.9 (4H, br,

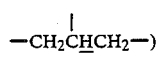

5.27 (4H, s, dioxole—CH$_2$—); 5.3~5.9 (1H, br,

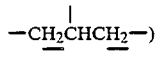

6.75 (2H, s, —H in position 3 of chromone nucleus); 6.95~7.35 (4H, m, —H in position 6 and in position 8 of chromone nucleus); 7.76 (2H, t, J=9 Hz, —H in position 7 of chromone nucleus); 7.0~10 (4H, br, —COOH, —NH$_3$+)

EXAMPLE 23

Synthesis of di(5-methyl-2-on-1,3-dioxol-4-ylmethyl)glycylcromoglycate hydrochloride Using BOC-glycine and proceeding in the same manner as in Example 22, there is obtained di(5-methyl-2-on-1,3-dioxol-4-ylmethyl) glycylcromoglycate hydrochloride.

IR (KBr, cm$^{-1}$) 1815, 1745, 1645:

NMR (DMSO-d$_6$, δ ppm): 2.22 (6H, s, dioxole—CH$_3$); 3.83 (2H, s, —CH$_2$NH$_3$+); 4.57 (4H, br.s,

5.25 (4H, s, dioxole—CH$_2$—); 5.4~5.95 (1H, br,

—CH$_2$CHCH$_2$—)

6.74 (2H, s, —H in position 3 of chromone nucleus); 6.9~7.38 (4H, m, —H in position 6 and in position 8 of chromone nucleus); 7.73 (2H, t, J=9 Hz, —H in position 7 of chromone nucleus); 8.0~8.9 (3H, br, —NH$_3$+)

EXAMPLE 24

Synthesis of di(5-methyl-2-on-1,3-dioxol-4-ylmethyl) L-alanylcromoglycate hydrochloride Using BOC-alanine and proceeding in the same manner as in Example 22, there is obtained di(5-methyl-2-on-1,3-dioxol-4-ylmethyl) L-alanylcromoglycate hydrochloride.

IR (KBr, cm$^{-1}$) 1815, 1740, 1650:

NMR (DMSO-d$_6$, δ ppm): 1.42 (3H, d, J=8 Hz,

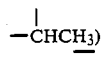

2.21 (6H, s, dioxole—CH$_3$); 4.1 (1H, q,

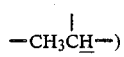

4.58 (4H, br.s,

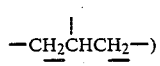

5.27 (4H, s, dioxole—CH$_2$—); 5.4~5.85 (1H, br,

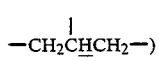

6.74, 6.77 (2H, s, —H in position 3 of chromone nucleus); 6.9~7.4 (4H, m, —H in position 6 and in position 8 of chromone nucleus); 7.73 (2H, t, J=9 Hz, —H in position 7 of chromone nucleus); 8.15~8.9 (3H, br, —NH$_3$+)

EXAMPLE 25

Synthesis of di(5-methyl-2-on-1,3-dioxol-4-ylmethyl) β-alanylcromoglycate hydrochloride Using BOC-β-alanine and proceeding in the same manner as in Example 22, there is obtained di(5-methyl-2-on-1,3-dioxol-4-ylmethyl) β-alanylcromoglycate hydrochloride.

IR (KBr, cm$^{-1}$) 1815, 1740, 1650:

NMR (DMSO-d$_6$, δ ppm): 2.22 (6H, s, dioxole—CH$_3$); 2.65~3.3 (4H, m, —CH$_2$CH$_2$—); 4.55 (4H, br.s,

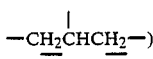

5.27 (4H, s, dioxole—CH$_2$—); 5.3~5.8 (1H, br,

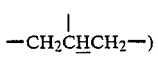

6.73 (2H, s, —H in position 3 of chromone nucleus); 6.85~7.4 (4H, m, —H in position 6 and in position 8 of chromone nucleus); 7.73 (2H, t, J=9 Hz, —H in position 7 of chromone nucleus); 7.7~8.45 (3H, br, —NH$_3$+)

EXAMPLE 26

Synthesis of di(5-methyl-2-on-1,3-dioxol-4-ylmethyl) L-prolylcromoglycate hydrochloride Using BOC-L-proline and proceeding in the same manner as in Example 22, there is obtained di(5-methyl-2-on-1,3-dioxol-4-ylmethyl) L-prolylcromoglycate hydrochloride.

IR (KBr, cm$^{-1}$) 1815, 1740, 1650:

NMR (DMSO-d$_6$, δ ppm): 1.5~2.7 (4H, m, —H$_2$ in position 3 and in position 4 of pyrrole ring) 2.23 (6H, s, dioxole—CH$_3$) 3.0–3.7 (2H, m, —H$_2$ in position 5 of pyrrole ring) 4.1~4.9 (5H, m,

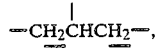

—H in position 2 of pyrrole ring) 5.25 (4H, s, dioxole—CH$_2$—) 5.4~5.9 (1H, br,

6.74, 6.76 (2H, s, —H in position 3 of chromone nucleus); 6.85~7.4 (4H, m, —H in position 6 and in position 8 of chromone nucleus); 7.73 (2H, t, J=9 Hz, —H in position 7 of chromone nucleus); 8.6~10.4 (2H, br,

EXAMPLE 27

Synthesis of di(1-ethoxycarbonyloxyethyl) β-alanylcromoglycate hydrochloride (1) DSCG (0.5 g) is added to 20 ml of DMF and, with ice cooling, 2 g of 1-iodoethyl carbonate is added dropwise over 2 hours. After further 2 hours of stirring, the reaction mixture is poured into 200 ml of water and extracted with ethyl acetate. The extract is washed with water and dried over sodium sulfate, and the solvent is then distilled off to give 256 mg of di(1-ethoxycarbonyloxyethyl) cromoglycate (yield 38%).

IR (nujol, cm$^{-1}$) 1765, 1660:

NMR (CDCl$_3$, δ ppm): 1.33 (6H, t, J=7 Hz, —CH$_2$CH$_3$); 1.67 (6H, d, J=6 Hz,

;
2.5~3.7 (1H, br, —OH); 4.24 (4H, q, J=7 Hz, —CH$_2$CH$_3$); 4.1~4.8 (5H, m,

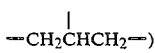

6.75–7.35 (8H, m,

—H in position 3, in position 6 and in position 8 of chromone nucleus); 7.59 (2H, t, J=9 Hz, —H in position 7 of chromone nucleus);

(2) The compound obtained in (1) is treated in the same manner as in Example 14 to give di(1-ethoxycarbonyloxyethyl) β-alanylcromoglycate hydrochloride.

IR (KBr, cm$^{-1}$) 1755, 1650:

NMR (DMSO-d$_6$, δ ppm): 1.25 (6H, t, J=7 Hz, —CH$_2$CH$_3$); 1.66 (6H, d, J=6 Hz,

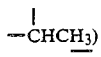

2.5~3.4 (4H, m, —CH$_2$CH$_2$—); 4.18 (4H, q, J=7 Hz, —CH$_2$CH$_3$); 4.55 (4H, br,

5.35~5.85 (1H, m,

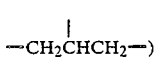

6.75 (2H, s, —H in position 3 of chromone nucleus); 6.8–7.35 (6H, m,

—H in position 6 and in position 8 of chromone nucleus; 7.71 (2H, t, J=9 Hz, —H in position 7 of chromone nucleus) 7.5~8.5 (2H, br, —NH$_3^+$)

Acute toxicity test

The cromoglycic acid derivatives produced in Examples 1, 4, 7, 11 and 12 were administered, each in the form of an aqueous solution, to groups of three ICR-strain male mice by the oral route. The results thus obtained are shown below in Table 1.

TABLE 1

| Example No. in which the compound was produced | LD$_{50}$ (mg/kg) |
|---|---|
| Example 1 | >1,000 |
| Example 4 | >1,000 |
| Example 7 | >1,000 |
| Example 11 | >1,000 |
| Example 12 | >1,000 |

Dosage Form Example 1

Tablets having the following composition were produced in the conventional manner.
Compound of Example 1: 5 mg
Polyvinylpyrrolidone: 20 mg
Starch: 75 mg
Magnesium stearate: 2 mg

Dosage Form Example 2

Tablets having the following composition were produced in the conventional manner.
Compound of Example 1: 10 mg
Tartaric acid: 50 mg Starch: 50 mg
Magnesium stearate: 3 mg

Dosage Form Examples 3

Tablets having the following composition were produced in the conventional manner.
Compound of Example 4: 20 mg
Starch: 50 mg
Hydroxypropylcellulose: 3 mg
Magnesium stearate: 5 mg

Dosage Form Example 4

The compound of Example 9 was admixed with citric acid and capsules were produced by using an ordinary capsule filling technique.
Compound of Example 9: 100 mg
Citric acid: 25 mg
Magnesium stearate: 1 mg

Dosage Form Example 5

Capsules having the following composition were produced in the same manner as in Dosage Form Example 4.
Compound of Example 1: 20 mg
Magnesium stearate: 2 mg
Lactose: To make the total weight 100 mg

Dosage Form Example 6

Dry syrup was produced in accordance with the following formulation.
Compound of Example 12: 50 mg
Citric acid: 25 mg
Sucrose: 70 mg
CMC-Na: 20 mg The compounds according to the invention were orally administered to rabbit in the form of an aqueous solution or suspension at a dose of 5 mg/kg and the urinary recovery rates (based on the corresponding quantities of cromoglycic acid) were determined by HPLC. The results obtained are shown below in Table 2.

TABLE 2

|  | 0–6 Hr urinary recovery (%) |
|---|---|
| Cromoglycic acid | 3.5 |
| Example 1 | 32.6 |
| Example 4 | 20.2 |
| Example 7 | 21.4 |
| Example 11 | 25.4 |

TABLE 2-continued

|  | 0–6 Hr urinary recovery (%) |
|---|---|
| Example 12 | 21.8 |

We claim:

1. A pharmacologically acceptable cromoglycic acid derivative of the general formula (I):

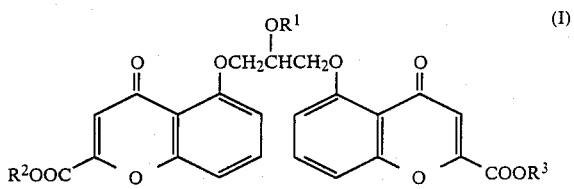

wherein $R^1$ is an $\alpha$-, $\beta$- or $\gamma$-amino acid residue (for ester bonding) whose amino group is optionally substituted by at least one lower alkyl group, and each of $R^2$ and $R^3$ is independently, a lower alkyloxy-substituted or an unsubstituted lower alkyl group, a 1-alkanoyloxyalkyl group, a 1-alkoxycarbonyloxyalkyl group, a phthalidyl group or a 5-methyl-1,3-dioxol-2-on-4-ylmethyl group; or a nontoxic salt thereof.

2. A cromoglycic acid derivative or a nontoxic salt thereof as claimed in claim 1, wherein the amino acid residue is lysyl, glycyl, alanyl, valyl or leucyl.

3. A cromoglycic acid derivative or a nontoxic salt thereof as claimed in claim 1, wherein each of $R^2$ and $R^3$ is methyl, ethyl, ethoxyethyl or 1-acetoxyethyl.

4. A cromoglycic acid derivative or a nontoxic salt thereof as claimed in claim 1, which is diethyl L-lysylcromoglycate dihydrochloride, diethyl glycylcromoglycate hydrochloride, diethy L-alanylcromoglycate hydrochloride or di(2-ethoxyethyl) L-lysylcromoglycate dihydrochloride.

5. A pharmaceutical anti-allergic composition which comprises a therapeutically effective amount of a cromoglycic acid derivative or a nontoxic salt thereof as claimed in claim 1 and pharmaceutically acceptable additive.

6. A method of increasing absorbability of cromoglycic acid through the digestive tract of a host in need of such therapy which comprises orally administering an antiallergic-effective amount of a compound of claim 1 to the host.

7. A method of increasing absorbability of cromoglycic acid through the digestive tract which comprises preparing a compound of claim 1.

8. A method for treating an allergic disease in a host afflicted with such disease, which comprises orally administering an effective amount of a compound of claim 1 to the host.

* * * * *

UNITED STATES PATENT AND TRADEMARK OFFICE
CERTIFICATE OF CORRECTION

PATENT NO. : 4,847,286

DATED : July 11, 1989

INVENTOR(S) : TAMAKI, et al.

It is certified that error appears in the above-identified patent and that said Letters Patent is hereby corrected as shown below:

Column 5, line 27, "carbocylic" should read --carboxylic--; line 28, "such" should read --, such--. Column 6, line 17, "-$CH_2CH_3$" should read -- -$CH_2CH_3$--; line 18, "-$CH_2NH$-" should read -- -$CH_2NH$- --; line 50, "-$CH_2CH_3$" should read -- -$CH_2CH_3$--; line 51, "-$CH_2NH_3^+$" should read -- -$CH_2NH_3^+$--; line 57, "-$CH_2CH_3$" should read -- -$CH_2CH_3$--. Column 7, line 12, "hydrochloirde" should read --hydrochloride--; line 15, "-$CH_2CH_3$" should read --$CH_2CH_3$-- and "-$CH_2NH_3^+$" should read -- -$CH_2NH_3^+$--; line 16, "-$CH_2CH_3$" should read -- -$CH_2CH_3$--. Column 8, line 10, "$cm^{-1}$" should read --$cm^{-1}$--; line 12, "-$CH_2CH_3$" should read -- -$CH_2CH_3$--; line 24, "-$CH_2C_3$" should read -- -$CH_2CH_3$--; line 51, "-$CH_2CH_3$-" should read -- -$CH_2CH_3$--; line 52, "-$CH_2CH_3$" should read -- -$CH_2CH_3$--. Column 9, line 11, "-$CH_2CH_3$" should read -- -$CH_2CH_3$--; line 17, "-$CH_2CH_3$" should read -- -$CH_2CH_3$-- and "-$CH_2NHCOCH_2$-" should read -- -$CH_2NHCOCH_2$- --; line 39, "-$CH_2CH_3$" should read -- -$CH_2CH_3$--; line 46, "-$COCH_2NH$-" should read -- -$COCH_2NH$- --; line 51, "-$CH_2CH_3$" should read -- -$CH_2CH_3$--; Column 10, line 12, "$CH(CH_3)_2$" should read -- -$CH(CH_3)_2$-- and "-$CH_2CH_3$" should read -- -$CH_2CH_3$--; line 20, "-$NHCH_2CO$-" should read -- -$NHCH_2CO$- --; line 26, "-$CH_2CH_3$" should read -- -$CH_2CH_3$--; line 54, "-$CH(CH_3)_2$" should read -- -$CH(CH_3)_2$-- and "-$CH_2CH_3$" should read -- -$CH_2CH_3$--; line 55, "-$CH(CH_3)_2$" should read -- -$CH(CH_3)_2$--; line 62, "-$CH_2CH_3$" should read -- -$CH_2CH_3$--. Column 11, line 19, "-$CH(CH_3)_2$" should read -- -$CH(CH_3)_2$-- and "-$CH_2CH_3$" should read -- -$CH_2CH_3$--; line 20, "-$CH_2CH(CH_3)_2$" should read -- -$CH_2CH(CH_3)_2$--; line 27, -$CH_2CH_3$" should read -- -$CH_2CH_3$--; line 59, "-$CH_2CH_3$" should read -- -$CH_2CH_3$--; line 60, "-$CH_2CH_3$" should read -- -$CH_2CH_3$--; line 61, "$H_2$" should read --$H_2$--. Column 12, line 8, "-$CH_2CH_3$" should read -- -$CH_2CH_3$--; lines 9 and 10, "-$CH_2CH_3$-" should read -- -$CH_2CH_3$--; line 10, "-$CH_2CH_2O$-" should read -- -$CH_2CH_2O$- --; line 44, "-$CH_2CH_3$" should read -- -$CH_2CH_3$--; line 50, "-$CH_2CH_3$" should read -- -$CH_2CH_3$--; line 51, "-$CH_2CH_2O$" should read -- -$CH_2CH_2O$--. Column 13, line 16, "-$CH_2CH_3$" should read -- -$CH_2CH_3$--; line 22, "-$CH_2CH_3$" should read -- -$CH_2CH_3$--;

UNITED STATES PATENT AND TRADEMARK OFFICE
CERTIFICATE OF CORRECTION

PATENT NO. : 4,847,286
DATED : July 11, 1989
INVENTOR(S) : TAMAKI, et al.

Page 2 of 2

It is certified that error appears in the above-identified patent and that said Letters Patent is hereby corrected as shown below:

line 23, "-$CH_2CH_2O$-" should read -- -$CH_2CH_2O$- --; line 30, "-$CH_2NH$" should read -- -$CH_2NH$- --; line 63, "4.0" should read --6H, m, -$(CH_2)_3$-); 2.9-3.2 (2H, m, -$CH_2NH$-); 4.0--. Column 14, line 28, "-$CH_2NH_3^+$" should read -- -$CH_2NH_3^+$ --. Column 16, line 6, "10H" should read --8H--; lines 35 and 36, "-$CH_2NHCOCH_2$-" should read -- -$CH_2NHCOCH_2$- --; line 48, "10 H" should read --8H--. Column 17 lines 6 and 7, "-$CH_2NHCOCH_2$-" should read -- -$CH_2NHCOCH_2$- --; line 54, "-$CH_2NH$-" should read -- -$CH_2NH$- --. Column 19, line 56, "-$CH_2NH_3^+$" should read -- -$CH_2NH_3^+$ --. Column 20, line 59, "CH)"

should read --$CH_3$)--; line 66, "m" should read --m, -$CH_2\underset{|}{C}HCH_2$-, -NH$\underline{CH}$-);--. Column 21, line 52, "-$CH_2NH_3^+$" should read -- -$CH_2NH_3^+$ --. Column 23, line 51, "-$CH_2CH_3$" should read -- -$CH_2CH_3$--; line 58, "-$CH_2CH_3$" should read -- -$CH_2CH_3$--. Column 24, line 9, "-$CH_2CH_3$" should read -- -$CH_2CH_3$--; line 16, -$CH_2CH_3$" should read -- -$CH_2CH_3$--. Column 26, line 19, "α" should read --α- --; line 22, "is" should read --is,--; line 36, "diethy" should read --diethyl--.

Signed and Sealed this

Twenty-fourth Day of September, 1991

Attest:

HARRY F. MANBECK, JR.

Attesting Officer

Commissioner of Patents and Trademarks